Oct. 3, 1961 D. H. MOREY, JR Plant Pat. 2,096
ROSE PLANT
Filed Nov. 25, 1960
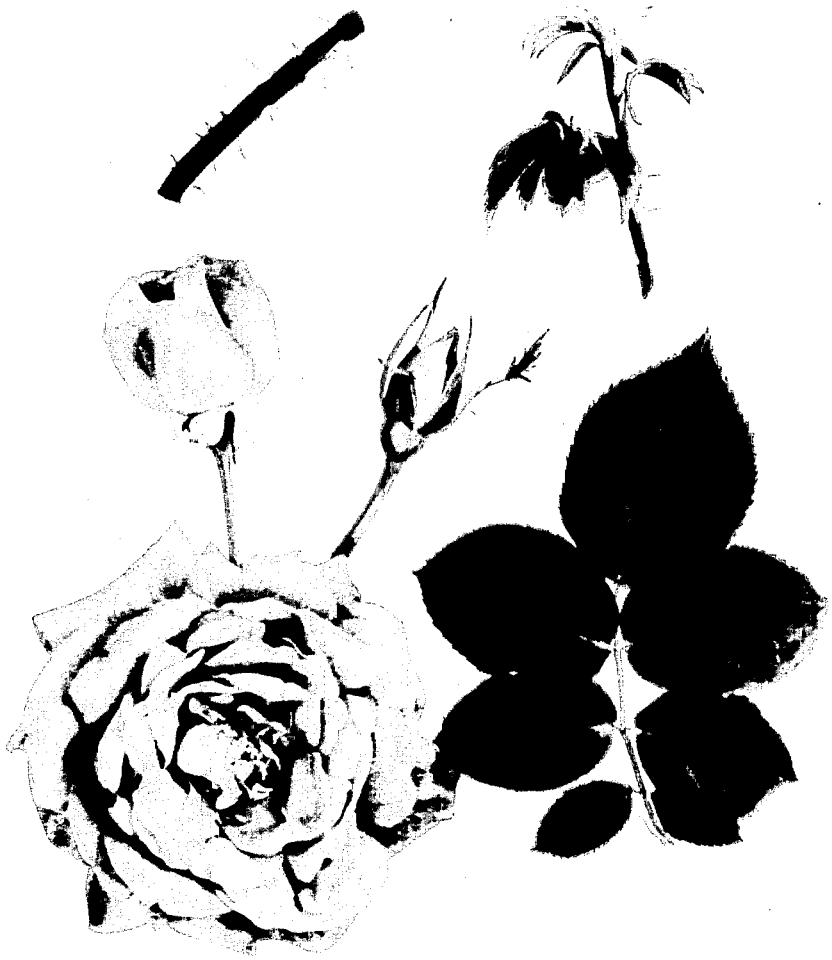
Inventor.
Dennison H. Morey, Jr
By: Robb & Robb
Attorneys.

United States Patent Office

Plant Pat. 2,096
Patented Oct. 3, 1961

2,096
ROSE PLANT

Dennison H. Morey, Jr., Pleasanton, Calif., assignor to Jackson & Perkins Company, Newark, N.Y., a corporation of New York Filed Nov. 25, 1960, Ser. No. 71,850
1 Claim. (Cl. 47—61)

The present invention relates to a new and distinct variety of rose plant of the hybrid tea class, which was originated by me by crossing the variety "Chrysler Imperial" (Plant Patent No, 1,167) with the variety "New Yorker" (Plant Patent No. 823).

The primary objective of this breeding was to produce a new red hybrid tea rose variety for out-of-door use. This objective was fully achieved, along with other desirable improvements, as evidenced by the following unique combination of characteristics which are outstanding in the new variety and which distinguish it from its parents, as well as from all other varieties of which I am aware:

(1) A distinctive and attractive Spectrum Red color tonality of the flowers;

(2) A cup-shaped flower form;

(3) A strong tea fragrance of the flowers; and (4) An unusual and peculiar arrangement of sepals on the half-open buds, wherein one sepal only is branched, and the others are smooth.

Asexual reproduction of the new variety by budding, as performed at Pleasanton, California, and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Chrysler Imperial."
*Pollen parent.*—"New Yorker."

Classification:
*Botanic.*—Hybrid tea.
*Commercial.*—Hybrid tea.

*Flower*

(Observations made from specimens grown outdoors at Newark, New York, about mid-afternoon in the latter part of the month of August.)

Blooming habit: Recurrent—continuous.

Bud:
*Size.*—Large.
*Form.*—Ovoid; is not affected by wet or hot weather.
*Color.*—When sepals first divide—Oxblood Red, Plate 1. When petals begin to unfurl—Carmine, Plate 1, lightly overcast with Nopal Red, Plate 1. When half-blown: inside of petals—Carmine, Plate 1; reverse of petals—Nopal Red, Plate 1, lightly overcast with Carmine, Plate 1.
*Sepals.*—Branched; curl back when petals begin to unfurl. Color: inside—Water Green, Plate 41; outside—Spinach Green, Plate 5, with tip end of sepals and branches Garnet Brown, Plate 13.
*Calyx.*—Color—Spinach Green, Plate 5. Shape—apple. Size—large. Aspect—smooth. Odor when rubbed—none.
*Peduncle.* — Length — medium. Aspect — smooth. Strength — erect; heavy. Color — Oil Green, Plate 5.
*Opening.*—Opens up well; is not affected by adverse weather conditions.

Bloom:
*Size.*—Large. Average size when fully expanded—4½ inches.
*Borne.*—Both singly and several together.
*Stems.*—Long; strong.
*Form (when first open).*—Cupped. Permanence—retains its form to the end.
*Petalage.*—Double (full but open center). Number of petals under normal conditions—30.
*Color.*—Center of flower—Carmine, Plate 1, lightly overcast with Scarlet-Red, Plate 1. Outer petals—Carmine, Plate 1, lightly overcast with Nopal Red, Plate 1. Base of petals (aiglet)—Pinard Yellow, Plate 4. Inside of petals—Spectrum Red, Plate 1. Reverse of petals—Nopal Red, Plate 1. General tonality from a distance—Spectrum Red, Plate 1.
*Discoloration.*—General tonality at end of first day—Carmine, Plate 1, lightly overcast with Scarlet-Red, Plate 1. Second day—Carmine, Plate 1, overcast with Spectrum Red, Plate 1. Third day—

Petals: Spectrum Red, Plate 1.
*Texture.*—Thick; is not affected by wet or hot weather.
*Appearance.*—Inside—velvety. Outside—satiny.
*Form.*—Oval.
*Arrangement.*—Imbricated (regularly arranged shingle-like).
*Petaloids in center.*—Few; small.
*Persistence.*—Drop off cleanly.
*Fragrance.*—Strong. Nature—tea (average hybrid tea scent).
*Lasting quality.*—On the plant—very long. As cut flower—very long.

*Genital organs*

Stamens, anthers: Medium size; many; regularly arranged around styles. Color—Light Salmon-Orange, Plate 2.

Stamens, filaments (threads): Medium length. Color—Alizarine Pink, Plate 13.

Pollen: Color—Orange Pink, Plate 2.

Styles: Bunched; uneven length; medium length; thin.

Stigmas: Color—Light Buff, Plate 15.

Ovaries: All enclosed in calyx.

Hips: None.

Seeds: None.

*Plant*

Form: Bush.

Growth: Vigorous; upright.

Foliage: Compound of 3–7 leaflets.
*Size.*—Large.
*Quantity.*—Normal.
*Color.*—New foliage: upper side—Garnet Brown, Plate 1; under side—Van Dyke Red, Plate 13. Old foliage: upper side—Dark Cress Green, Plate 31; under side—Light Bice Green, Plate 27.
*Shape.*—Oval.
*Texture.*—Upper side—leathery. Under side—smooth.
*Ribs and veins.*—Ordinary.
*Edge.*—Serrated (saw-toothed).
*Serrations.*—Both double and single; small.
*Leaf stem.*—Color—Courge Green, Plate 17. Under side—prickly.
*Stipules.*—Medium length; smooth.

Wood:

*New wood.*—Color—Cedar Green, Plate 6. Bark—smooth.

*Old wood.*—Color—Lincoln Green, Plate 41. Bark—smooth.

Thorns:

*Thorns.*—Quantity: on main stalks from base—many; on laterals from stalk—many. Form—flat base; medium length; straight. Color (when young) — Old Rose, Plate 13. Position — irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a distinctive and attractive Spectrum Red general color tonality of the flowers, a cupped flower form, strong tea fragrance of the flowers, and an unusual and peculiar arrangement of the sepals on the half-open buds, wherein one sepal only is branched and the others are smooth.

No references cited.